United States Patent [19]

Bartels

[11] Patent Number: 5,009,783

[45] Date of Patent: Apr. 23, 1991

[54] SEPARATION OF COMPOSITIONS CONTAINING WATER AND ORGANIC OXYGENATES

[75] Inventor: Craig R. Bartels, Wappinger Falls, N.Y.

[73] Assignee: Texaco Inc., White Plains, N.Y.

[21] Appl. No.: 533,223

[22] Filed: Jun. 4, 1990

Related U.S. Application Data

[62] Division of Ser. No. 456,619, Jan. 2, 1990.

[51] Int. Cl.$^5$ .............................................. B01D 69/00
[52] U.S. Cl. ............................ 210/500.41; 252/62.3 R
[58] Field of Search ..................... 252/62.3 R, 62.3 Q; 210/500.21, 500.1, 500.27, 500.41

[56] References Cited

U.S. PATENT DOCUMENTS 4,664,669  5/1987  Ohyabu et al. ................. 210/500.21

Primary Examiner—Frank Sever
Attorney, Agent, or Firm—Robert A. Kulason; James J. O'Loughlin; Carl G. Seutter

[57] ABSTRACT

Water is separated from aqueous mixtures of organic oxygenates such as isopropanol by pervaporation through a non-porous separating membrane of a blend of polyvinyl alcohol and a polyacrylic acid mounted on a polysulfone porous support layer.

4 Claims, No Drawings

SEPARATION OF COMPOSITIONS CONTAINING WATER AND ORGANIC OXYGENATES

This is a division of application Ser. No. 07/459,619 filed Jan. 2, 1990, now pending.

RELATED APPLICATIONS

Application Ser. No. 07/214,987 filed July 5, 1988, of Mordechai Pasternak, Craig R. Bartels, and John Reale, Jr. is directed to the separation of water from a hydrocarbon mixture with an organic oxygenate by the use of membrane technology.

FIELD OF THE INVENTION

This invention relates to the dehydration of organic oxygenates such as alcohols. More particularly it relates to a membrane technique for effecting separation of water from an aqueous mixture containing alcohols such as isopropyl alcohol.

BACKGROUND OF THE INVENTION

As well known to those skilled in the art, it is possible to remove water from mixtures thereof with organic liquids by various techniques including adsorption or distillation. These conventional processes, particularly distillation, are however, characterized by high capital cost. In the case of distillation for example the process requires expensive distillation towers, heaters, heat exchangers (reboilers, condensers, etc.), together with a substantial amount of auxiliary equipment typified by pumps, collection vessels, vacuum generating equipment, etc.

Such operations are characterized by high operating costs principally costs of heating and cooling —plus pumping, etc.

Furthermore the properties of the materials being separated, as is evidenced by the distillation curves, may be such that a large number of plates may be required, etc. When the material forms an azeotrope with water, additional problems may be present which for example, may require that separation be effected in a series of steps (e.g. as in two towers) or by addition of extraneous materials to the system.

There are also comparable problems which are unique to adsorption systems.

It has been found to be possible to utilize membrane systems to separate mixtures of miscible liquids by pervaporation. In this process, the charge liquid is brought into contact with a membrane film; and one component of the charge liquid preferentially permeates the membrane. The permeate is then removed as a vapor from the downstream side of thee film —typically by sweeping with a carrier gas or by reducing the pressure below the vapor pressure of the permeating species.

Illustrative membranes which have been employed in prior art techniques include those set forth in the following table:

TABLE

| Separating Layer | References |
| --- | --- |
| Nafion brand of perfluorosulfonic acid | Cabasso and Liu J. Memb. Sci. 24, 101 (1985) |
| Sulfonated polyalkylene | USP 4,728,429 to Cabasso et al |
| Sulfonated polyethylene | Cabasso, Korngold & Liu J. Pol. Sc: Letters, 23, 57 (1985) |
| Fluorinated polyether or Carboxylic Acid fluorides | USP 4,526,948 to Dupont as assignee of Resnickto |
| Selemion AMV brand of Asahi Glass cross-linked styrene butadiene (with quaternary ammonium residues on a polyvinyl chloride backing) | Wentzlaff Boddeker & Hattanbach J. Memb. Sci. 22,333 (1985) |
| Cellulose triacetate | Wentzlaff, Boddeker & Hattanback, J. Memb. Sci. 22, 333 (1985) |
| Polyacrylonitrile | Neel, Aptel & Clement Desalination 53, 297 (1985) |
| Crosslinked Polyvinyl Alcohol | Eur. Patent 0 096 339 to GFT as assignee of Bruschke |
| Poly(maleimide-acrylonitrile) | Yoshikawa et al J. Pol. Sci., 22,2159 (1984) |
| Dextrine isophoronediisocyanate | Chem. Econ. Eng. Rev., 17, 34 (1985) |

The cost effectiveness of a membrane is determined by the selectivity and productivity. Of the membranes commercially available, an illustrative membrane of high performance is that disclosed in European patent 0 096 339 A2 of GFT as assignee of Bruschke - published 21 Dec. 1983.

European Patent 0 096 339 A2 to GFT as assignee of Bruschke discloses, as cross-linking agents, diacids (typified by maleic acid or fumaric acid); dihalogen compounds (typified by dichloroacetone or 1,3-dichloroisopropanol); aldehydes, including dialdehydes, typified by formaldehyde. These membranes are said to be particularly effective for dehydration of aqueous solutions of ethanol or isopropanol.

This reference discloses separation of water from alcohols, ethers, ketones, aldehydes, or acids by use of composite membranes. Specifically the composite includes (i) a backing typically about 120 microns in thickness, on which is positioned (ii) a microporous support layer of a polysulfone or a polyacrylonitrile of about 50 microns thickness, on which is positioned (iii) a separating layer of cross-linked polyvinyl alcohol about 2 microns in thickness.

Polyvinyl alcohol may be cross-linked by use of difunctional agents which react with the hydroxyl group of the polyvinyl alcohol. Typical cross-linking agent may include dialdehydes (which yield acetal linkages), diacids or diacid halides (which yield ester linkages), dihalogen compounds or epichlorhydrin (which yield ether linkages) olefinic aldehydes (which yield ether/acetal linkages), boric acid (which yields boric ester linkages), sulfonamidoaldehydes, etc.

See also J. G. Prichard, *Polyvinyl Alcohol, Basic Properties and Uses.* Gordon and Breach Science Publishers, New York (1970) or C. A. Finch, *Polyvinyl Alcohol, Properties and Applications,* John Wiley and Sons, New York (1973).

T. Q. Nguyen et al *Synthesis of Membranes for the Dehydration of Water-Acetic Acid Mixtures by Pervaporation* Makromol. Chem 188, 1973–1984 (1987).

H. Karakane et al *Separation of Water-Ethanol by Pervaporation Through Polyelectrolyte Complex Compos-*

*ite Membrane.* Proc. Third Int. Cont. on Pervaporation Processes in the Chemical Industry, Nancy, France Sep 19-22, 1988.

U.S. Pat. No. 4,755, 299 to BrusChke, U.S. Pat. 4,802,988 to Bartels and Reale, Jr., U.S. Pat. No. 4,728,429 to Cabasso et al, U.S. Pat. No. 4,067,805 to Chiang et al, U.S. Pat. 4,526,948 to Resnick, U.S. Pat No. 3,750,735 to Chiang et al, and U.S. Pat. No. 4,690,766 to Linder et al provide additional background.

It is an object of this invention to provide a novel composite membrane characterized by its ability to effect separation of water from organic oxygenates such as isopropyl alcohol. Other objects will be apparent to those skilled in the art.

STATEMENT OF THE INVENTION

In accordance with certain of its aspects, this invention is directed to a method of separating a charge aqueous composition containing organic oxygenate selected from the group consisting of alcohols, glycols, and weak acids which comprises maintaining a non-porous membrane separating layer of a blend of a polyvinyl alcohol and a polyacrylic acid mounted on a polysulfone porous support layer;

maintaining a pressure drop across said non-porous membrane separating layer;

passing an aqueous charge composition containing water and organic oxygenate selected from the group consisting of alcohols, glycols, and weak acids into contact with the high pressure side of said non-porous separating layer whereby at least a portion of said water in said aqueous charge mixture and a lesser portion of organic oxygenate pass by pervaporation through said non-porous separating layer as a lean mixture containing more water and less organic oxygenate selected from the group consisting of alcohols, glycols, and weak acids than are present in said aqueous charge and said charge is converted to a rich liquid containing less water and more organic oxygenate selected from the group consisting of alcohols, glycols, and weak acids than are present in said aqueous charge;

recovering from the low pressure side of said nonporous separating layer said lean mixture containing more water and less organic oxygenate selected from the group consisting of alcohols, glycols, and weak acids than are present in said aqueous charge, said lean mixture being recovered in vapor phase at a pressure below the vapor pressure thereof; and recovering from the high pressure side of said non-porous separating layer said rich liquid containing a lower water content and more organic oxygenate selected from the group consisting of alcohols, glycols, and weak acids than are present in said charge.

DESCRIPTION OF THE INVENTION

The composite structure of this invention includes a multi-layer assembly which in the preferred embodiment preferably includes a porous carrier layer which provides mechanical strength and support to the assembly.

THE CARRIER LAYER

This carrier layer, when used, is characterized by its high degree of porosity and mechanical strength. It may be fibrous or non-fibrous, woven or non-woven. In the preferred embodiment, the carrier layer may be a porous, flexible, non-woven fibrous polyester.

A preferred non-woven polyester carrier layer may be formulated of non-woven, thermally-bonded strands and characterized by a fabric weight of 80±8 grams per square yard, a thickness of 4.2±0.5 mils, a tensile strength (in the machine direction) of 31 psi and (in cross direction) of 10 psi, and a Frazier air permeability of 6 cuft/min/sq. ft. @ 0.5 inches of water.

THE POROUS SUPPORT LAYER

The porous support layer which may be used in practice of this invention is (preferably) formed of a sheet of polysulfone polymer. Typically the polysulfone may be of thickness of 40-80 microns, say 50 microns and of molecular weight $\overline{M}^n$ of 5,000-100,000, preferably 20,000-60,000 say 40,000. The polysulfone is preferably characterized by a pore size of less than about 500Å and typically about 200A. This corresponds to a molecular weight cut-off of less than about 25,000 typically about 20,000.

The sulfone polymers which may be employed may include those made from cumene, containing isopropylidene groups in the backbone; e.g.

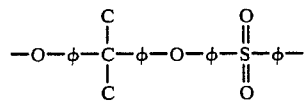

These isopropylidene sulfones containing repeating units including ether-aromatic-isopropylidene-aromatic-etheraromatic-sulfone-aromatic groups may typically have a molecular weight $\overline{M}^n$ of 15,000-30,000, a water absorption (at 20° C.) of about 0.85 w%, a glass transition temperature of 449.K, a density of 1.25 g/cm³, a tensile strength (at 20° C.) at yield of 10,000 psi, and a coefficient of linear thermal expansion of $2.6 \times 10^{-5}$ mm/mm/° C.

It is found, however, that the preferred sulfone polymers which may be employed in practice of the process of this invention, may include those which are free of isopropylidene moieties in the backbone chain and wherein the phenylene groups in the backbone are bonded only to ether oxygen atoms and to sulfur atoms One preferred polymer, which may typically, be prepared from

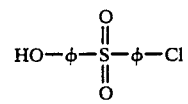

may be characterized by a backbone containing the following repeating groups:

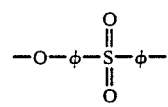

A preferred sulfone polymer may be a polyether sulfone which is free of isopropylidene moieties in the backbone chain and wherein the phenylene groups in the backbone are bonded only to ether-oxygen atoms and to sulfur atoms. This polymer may be characterized by molecular weight $\overline{M}^n$ of 25,000, water absorption @ 20° C. wt. 2.1 w, glass transition temperature of 487° K, tensile strength at yield of 12,200 psig at 20° C.; and coefficient of linear thermal expansion of $5.5 \times 10^{-5}$ mm/mm/°C. This polymer has a molecular weight cut off of about 20,000 and has a pore size of about 200Å.

THE SEPARATING LAYER

In accordance with certain of its aspects, the separating layer may be a blend or mixture of vinyl alcohol polymer and a polymer of an acrylic acid such as acrylic acid or methacrylic acid. The charge from which this separating membrane may be prepared may be an aqueous solution containing a vinyl alcohol polymer and a polymer of an acrylic acid. Typically the aqueous solution may contain 5–10w%, say 7w% of polyvinyl alcohol of molecular weight $\overline{M}^n$ of 20,000, 200,000, say 115,000 and 5–10lw%, say 7w% of polyacrylic acid of molecular weight $\overline{M}_n$ of 90,000–300,000 say 250,000. The weight ratio of vinyl alcohol polymer to acrylic acid polymer may be 0.1–10:1, say 1:1. Generally desirably higher Flux is attained by use ratios e.g. 0.1–0.5, say 0.25.

When the separating layer is prepared from a mixture of vinyl alcohol polymer and acrylic acid polymer (as in a preferred embodiment) it is desirable to mix the aqueous solutions of polymers to form a mix containing both polymers.

The composite membrane, prepared from the blend of polyvinyl alcohol and polyacrylic acid, may then be cured in an oven at 125° C–225° C., preferably 150° C.–225° C., say 150° C. for 1–30 minutes, say 10 minutes to yield a membrane of polyvinyl alcohol-polyacrylic acid film having a thickness of 1–10 microns, say 2 microns. During heating for the noted time, it appears that the components of the membrane system react or interact to internally cure or cross-link the system; and no external curing agent is needed. In fact, presence of external curing agents denigrates against performance of the membranes.

During curing, the polyvinyl alcohol and the polyacrylic acid may crosslink or otherwise react to form ester linkages. It also appears that the separating layer may interact with the polysulfone support layer to form a system characterized by unexpectedly high flux.

Illustrative polyvinyl alcohol-polyacrylic acid membranes which may be employed may include:

TABLE

I. The membrane prepared by casting a mixture of equal parts by weight of a 7 w% solution of polyvinyl alcohol of $\overline{M}_n$ of 115,000 and a 7 w% solution of polyacrylic acid of $\overline{M}_n$ of 250,000, the mixture after casting being cured at 150° C. for 10 minutes to yield a film of about 2 microns thick.

II. The membrane prepared bY mixing equal parts of a 7 w% aqueous suspension of polyvinyl alcohol of $\overline{M}_n$ of 115,000 and a 7 w% aqueous suspension of polyacrylic acid of $\overline{M}hd n$ of 250,000 and casting the mixture, followed by curing at 140° C. for 15 minutes to form a film of thickness about 2.5 microns.

III. The membrane prepared by mixing equal parts of a 6 w% aqueous suspension of polyvinyl alcohol of $\overline{M}_n$ of 100,000 and a 7 w% aqueous suspension of polymethacrylic acid of $\overline{M}_n$ of 280,000 and casting the mixture followed by curing at 150 C for 10 minutes to yield a film of thickness of about 2 microns.

THE COMPOSITE MEMBRANE

It is a feature of this invention that the composite membrane of this invention may comprise (i) an optional carrier layer, characterized by porosity and mechanical strength, for supporting a porous support layer and a separating layer, (ii) a polysulfone porous support layer of molecular weight cutoff of 20,000–40,000 and (iii) mounted thereon as a non-porous separating layer a blend of polyvinyl alcohol of molecular weight 20,000 –200,000 and, say 115,000 and polyacrylic acid of molecular weight 50,000–350,000, say 250,000.

The composite membrane of this invention may be utilized in various configurations It is, for example, possible to utilize the composite in a plate-and-frame configuration in which separating layers may be mounted on the porous support layer with the carrier layer.

It is possible to utilize a spiral wound module which includes a non-porous separating layer membrane mounted on a porous support layer and carrier layer, the assembly being typically folded and bonded or sealed along all the edges but an open edge–to form a bag-like unit which preferably has the separating layer on the outside. A cloth spacer, serving as the membrane or discharge channel is placed within the bag-like unit The discharge channel projects from the open end of the unit.

There then placed on one face of the bag-like unit, adjacent to the separating layer, and coterminous therewith, a feed channel sheet—typically formed of a plastic net.

The so-formed assembly is wrapped around a preferably cylindrical conduit which bears a plurality of perforations in the wall–preferably in a linear array which is as long as the width of the bag-like unit. The projecting portion of the discharge channel of the bag-like unit is placed over the perforations of the conduit; and the bag-like unit is wrapped around the conduit to form a spiral wound configuration.

It will be apparent that, although only one feed channel is present, the single feed channel in the wound assembly will be adjacent to two faces of the membrane layer. The spiral wound configuration may be formed by wrapping the assembly around the conduit a plurality of times to form a readily handleable unit The unit is fitted within a shell (in manner comparable to a shell-and-tube heat exchanger) provided with an inlet at one end and an outlet at the other. A baffle-like seal between the inner surface of the shell and the outer surface of the spiral-wound input prevents fluid from bypassing the operative membrane system and insures that fluid enters the system principally at one end. The permeate passes from the feed channel, into contact with the separating layer and thence therethrough, into the permeate channel and thence therealong to and through the perforations in the conduit through which it is withdrawn as net permeate.

In use of the spiral wound membrane, charge liquid is permitted to pass through the plastic net which serves as a feed channel and thence into contact with the non-porous separating membranes. The liquid which does not pass through the membranes is withdrawn as retentate. The liquid or vapor which permeates the membrane passes into the volume occupied by the permeate spacer and through this permeate channel to the perforations in the cylindrical conduit through which it is withdrawn from the system. In this embodiment, it will be apparent that the system may not include a carrier layer.

In another embodiment, it is possible to utilize the system of this invention as a tubular or hollow fibre. In this embodiment, the polysulfone porous support layer may be extruded as a fine tube with a wall thickness of typically 0.001–0.mm. The extruded tubes are passed through a bath of polyvinyl alcohol/polysulfone which is cured in situ. A bundle of these tubes is secured (with an epoxy adhesive) at each end in a header; and the fibres are cut so that they are flush with the ends of the header. This tube bundle is mounted within a shell in a typical shell-and-tube assembly.

In operation, the charge liquid is admitted to the tube side and passes through the inside of the tubes and exits as retentate. During passage through the tubes, permeate passes through the non-porous separating layer and permeate is collected in the shell side.

In this embodiment, it will be apparent that the system may not normally include a carrier layer. In still another embodiment, the porous support layer may be omitted; and the separating layer is extruded and thereafter crosslinked and cured in situ prior to mounting in the headers.

PERVAPORATION

It is a feature of the non-porous polyvinyl alcohol—polyacrylic acid separating layer on polysulfone support that it is found to be particularly effective when used in a pervaporation process. In pervaporation, a charge liquid containing a more permeable and a less permeable component is maintained in contact with a non-porous separating layer; and a pressure drop is maintained across that layer. The charge liquid dissolves into the membrane and diffuses therethrough. The permeate which passes through the membrane and exits as a vapor may be recovered by condensing at low temperature or alternatively may be swept away by use of a moving stream of gas Preferably, the permeate side of the membrane is maintained at a low pressure, typically 5 mm. Hg.

For general background on pervaporation, note U.S. Pat. No. 4,277,344; U.S. Pat. No. 4,039,440; U.S. Pat. No. 3,926,798; U.S. Pat. No. 3,950,247; U.S. Pat. No. 4,035,291; etc.

It is a feature of the process of this invention that the novel membrane may be particularly useful in pervaporation processes for dewatering aqueous mixtures of organic oxygenates selected from the group consisting of alcohols, glycols, and weak acids It will be apparent to those skilled in the art that it may be desirable to separate large quantities of water from partially miscible systems as by decantation prior to utilizing the process of the invention to remove the last traces of water.

The advantages of the instant invention are more apparent when the charge liquid is a single phase homogenous aqueous solution as is the case for example with isopropanol. It is also a feature of this invention that it may be particularly useful to separate azeotropes such as isopropanol-water.

The charge organic oxygenates which may be treated by the process of this invention may include alcohols, glycols, and weak acids. It will be apparent to those skilled in the art that the charge organic oxygenates used should be inert with respect to the separating membrane. Clearly a system wherein the membrane is attacked by the components of the charge liquid will not yield significant separation for any reasonable period of time. Best results may be achieved when treating alcohols (such as isopropanol) or glycols (such as ethylene glycol) Results achieved with acids are generally less satisfactory.

Illustrative alcohols may include ethanol, propanol, n-butanol, i-butanol, t-butanol, amyl alcohols, hexyl alcohols, etc.

Illustrative glycols may include ethylene glycol, propylene glycol, butylene glycol or glycol ethers such as diethylene glycol, triethylene glycol, or triols, including glycerine; etc.

Illustrative weak acids may include formic acid, oxalic acid, acetic acid, propionic acid, etc.

It is believed that the advantages of this invention are most apparent where the organic oxygenate is a liquid such as isopropanol which in preparation or in use may pick up quantities of water from various sources.

A typical charge may be an aqueous mixture containing 70%–99%, say about 95% isopropanol.

In practice of the pervaporation process of this invention, the charge aqueous organic oxygenate aqueous solution typically at 40° C.–90° C., say 65° C. may be passed into contact with the non-porous separating layer of the membrane of this invention. A pressure drop of about one atmosphere is commonly maintained across the membrane. Typically, the feed or charge side of the membrane is at about atmospheric pressure and the permeate or discharge side of the membrane is at a pressure of about 2–50 preferably 5–20, say 5 mm. Hg.

The permeate which passes through the membrane includes water and a small proportion of the organic oxygenate form the charge liquid. Typically, the permeate contains 95–99, say 98 w% water. Permeate is recovered in vapor phase.

Pervaporation may typically be carried out at a Flux of 0.1–3 say 0.22 kilograms per square meter per hour (kmh). Typically, the units may show good separation (measured in terms of w% organic oxygenate in the permeate during pervaporation of an aqueous solution of organic oxygenate through a polyvinyl alcohol polyacrylic acid separating layer on a polysulfone support).

It will be apparent that the preferred membrane is one which gives good separation (i.e. low concentration of oxygenate in the permeate) and high Flux. It is a particular feature of the process of this invention that it yields good Separation at a Flux which may be as great as ten times and commonly 5–6 times that attained when using e.g. a polyacrylonitrile support layer.

The Separation Factor S or Sep which represents the ability of the membrane to separate water is calculated as follows:

$$S = \frac{\left(\frac{X_n}{X_m}\right)_p}{\left(\frac{X_n}{X_m}\right)_f}$$

wherein $X_n$ and $X_m$ are the weight fractions of water and non-aqueous components respectively in the permeate (P) and the feed (F). A system showing no separation at all would have a Separation Factor of 1; and a system showing perfect 100% separation would have a Separation Factor of infinity. The process of the instant invention may have a Separation Factor of as high as 1400—typically several hundred up to, say about 300. Satisfactory operation may require a Separation Factor of at least about 1000 (this may vary substantially) although good commercial practice may require Separation Factors which are higher. The process of this invention typically yields Separation Factors which are satisfactory.

Practice of the process of this invention will be apparent to those skilled in the art from inspection of the following examples wherein, as elsewhere in this specification, all parts are parts by weight unless otherwise stated. An asterisk (*) indicates a control example

DESCRIPTION OF SPECIFIC EMBODIMENTS

EXAMPLE I

In this example, which represents the best mode presently known of carrying out the process of this invention, the selective separating layer is mounted on a porous support layer of a commercially available composite containing a non-woven polyester backing as carrier layer, bearing as porous support layer, a microporous membrane of a polyether sulfone which is free of isopropylidene moieties in the backbone chain and wherein the phenylene groups in the backbone are bonded only to ether-oxygen atoms and to sulfur atoms. This polymer may be characterized by molecular weight $\overline{M}_n$ of 25,000, water absorption @ 20° C. of 2.1 w%, glass transition temperature of 487° K., tensile strength at yield of 12,200 psig at 20.C; and coefficient of linear thermal expansion of $5.5 \times 10^{-5}$ mm/mm/° C. This polymer has a molecular weight cut-off of about 20,000 and has pore size of about 200Å.

The separating layer is formed by mixing equal parts of weight of (i) a 7w% aqueous solution of polyvinyl alcohol PVA of molecular weight $\overline{M}_n$ of 115,000 and (ii) a 7w% aqueous solution of polyacrylic acid PAA of molecular weight $\overline{M}_n$ of 250,000. The mix is spread on the support to form a film which is then cured at 150° C. for 15 minutes.

The membrane is evaluated in a pervaporation cell to which the charge is admitted at 70.C. Permeate pressure is <5 mm.Hg at liquid nitrogen temperature.

In this preferred embodiment, the charge solution contains 95.1 w% isopropanol (IPA) 4.9w% water. The permeate condenser contains an aqueous solution containing only 5.8w% IPA. The Flux (kmh) is 0.22. The Separation Factor is 315.

EXAMPLE II*

In this Control Example, the porous support layer is a polyacrylonitrile membrane of thickness of about 50 microns having a molecular weight cut-off of about 40,000. The separating layer and the carrier layer are the same as in Example I. Other conditions are as in Example I.

In Example II*, the charge contains 97.4 w% IPA and 2.6 w% water—which is comparable to the charge of Example I.

The Flux (kmh) attained in Example II* is only 0.04 kmh (at a permeate concentration of 0.2 w% IPA).

From these Examples, it may be seen that use of the polysulfone membrane of this invention unexpectedly permits attainment of Flux which is (0.22/0.04 or) 5.5 times higher than is attained when using the control polyacrylonitrile membrane.

EXAMPLES III-XI

In this series of Examples, the procedure of Example I is carried out using the membrane system of that example except:

(i) The separating membrane is 100% PVA/0% PAA in Example III*, 70% PVA/30% PAA in Example IV, and 50% PVA/50% PAA in all other Examples.

(ii) The PVA—containing membrane is cross-linked (at 125° C. for 15 minutes) with glutaraldehyde in mole ratio (of glutaraldehyde to PVA) of 0.2 (in Control Example III* and VII*) and of 0.4 (in Control Example VI*) and of 0.04 (in Control Example VIII*).

(iii) Curing Temperature (°C) is 100° C. (in Example IX), 125° C. (in Examples III*, VI*, VIII*, and X) 150° C. (in Examples I, II, IV, and V), and 125° C. (in Example XI)

TABLE

| Example | PVA/PAA W Ratio | Feed Conc % IPA | Perm Conc % IPA | Sep | Flux (Kmh) |
|---|---|---|---|---|---|
| III* | 100/0 | 95.8 | 0.04 | 57,000 | 0.04 |
| IV | 70/30 | 95.2 | 29.8 | 46 | 0.09 |
| V | 50/50 | 95.8 | 7.1 | 298 | 0.19 |
| VI* | 50/50 | 96.7 | 6.5 | 422 | 0.01 |
| VII* | 50/50 | 96.7 | 0.5 | 5830 | 0.02 |
| VIII* | 50/50 | 96.7 | 3.0 | 947 | 0.06 |
| IX* | 50/50 | 95.1 | 87.4 | 3 | 2.6 |
| X | 50/50 | 95.1 | 45 | 24 | 0.70 |
| I | 50/50 | 95.1 | 5.8 | 315 | 0.22 |
| XI | 50/50 | 95.1 | 1.4 | 1370 | 0.14 |
| II* | 50/50 | 97.4 | 0.2 | 18,700 | 0.04 |

From the above Table, it is apparent that:

(i) Experimental Example I, which gives the highest Flux (0.22 kmh), at low concentration of IPA in the permeate, is carried out using a 50/50 PVA/PAV separating membrane on a polysulfone support—the separating membrane being cured at 150° C. with no external cross-linking;

(ii) Control Example II* which is generally comparable to Experimental Example I, (except that Example II* uses a polyacrylonitrile support layer whereas Example I uses a polysulfone support layer) gives Flux which are only (0.04/0.22 or) 18% of those attained in Example I;

(iii) Control Example III*, VI* VIII* which utilize "external" cross-linking with glutaraldehyde, yield undesirably low Flux (0.04–0.01—0.02-0.06) in contrast to e.g. Experimental Example I (0.22) which utilizes internal cross-linking;

(iv) Comparison of Experimental Examples IX, X, I, and XI show that as the curing temperature increases over the 100° C.-175° C. range, the Flux drops and the concentration of IPA in the permeate also drops. A balance between these two factors indicates that Example I shows best promise as a candidate for further consideration.

(v) Example IX* shows inter alia that a temperature of 100.C (87.6 w% IPA in the permeate) is not high enough to cure the system properly. Curing should be done at 125.C or above and preferably 150° C.-225° C., say 150° C.

EXAMPLES XII-XIX

In this series of Examples, the effect of time on membrane performance is measured. In each case, the membrane is prepared as in Example I except that the weight percent of PAA in the membranes is varied (the remainder being PVA) and the curing conditions are varied. The Selectivity (w% IPA in the permeate) and the Flux (kmh) at 0 time and at greater than 48 hours are measured Feed is 85 w% IPA at 70° C.

TABLE

| Example | Memb W% PAA | Curing T/t | Initial Performance Sel | Initial Performance Flux | Final Performance Sel | Final Performance Flux |
|---|---|---|---|---|---|---|
| XII | 80 | 150° C./4 min | 77 | 2.7 | 4.0 | 0.78 |
| XIII | 60 | " | 54 | 2.1 | 5.2 | 0.83 |
| XIV | 40 | " | 11 | 1.3 | 1.7 | 0.69 |
| XV | 20 | " | 5.8 | 0.86 | 0.39 | 0.56 |
| XVI | 80 | 150° C./10 min | 64 | 2.6 | 2.5 | 0.84 |
| XVII | 60 | " | 19 | 1.7 | 2.8 | 0.89 |
| XVIII | 40 | " | 6.8 | 1.2 | 2.4 | 0.87 |
| XIX | 20 | " | 1.3 | 0.6 | 0.37 | 0.50 |

From the above Table, it is apparent that:

(i) Practice of this invention gives good Flux and Selectivity both initially and finally (after 48 hours);

(ii) Selectivity generally improves over time while Flux generally drops over time;

(iii) Best initial Flux (of 2.7) is attained using the 80/20 membrane cured at 150.C for 4 minutes; and the Flux is high (0.78) at the end of the test;

(iv) Best Final Flux (0.89) is attained with 60/40 membrane cured at 150° C. for 10 minutes.

It is a feature of this invention that the desired results are attained by internal (or intermolecular) cross-linking by the reaction or interaction of the PVA and the PAA and the polysulfone (PS) on/with each other—as distinguished from the external cross-linking of the prior art (e.g. glutaraldehyde) cross-linking agents. It appears the PAA (of higher molecular weight) contributes acid functionality which aids the cross-linking with the PVA. The PAA apparently also retains unreacted carboxylic acid functionalities which impart a hydrophilic character to the final membrane. The product membrane is internally crosslinked; and this contributes to its ability to dewater solutions at higher temperature which would normally dissolve PAA or PAA (q.v. the uncross-linked membrane of Nguyen loc cit.)

Although this invention has been illustrated by reference to specific embodiments, it will be apparent to those skilled in the art that various charges and modifications may be made which clearly fall within the scope of the invention.

What is claimed is:

1. A composition comprising as a composite at least having properties for enabling pervaporation of a charge aqueous composition containing organic oxygenate selected from the group consisting of alcohols, glycols and weak acids, including:

(i) a polysulfone membrane as a porous support layer; and (ii) mounted thereon, as a non-porous separating layer, a blend of a polyvinyl alcohol and a polyacrylic acid.

2. A composition as claimed in claim 1 which has been cured at 125° C. -225° C. for 1-30 minutes.

3. A composition as claimed in claim 1 which has been cured at 150° C-225° C. for 1-30 minutes.

4. A composition comprising as a composite at least having properties for enabling pervaporation of a charge aqueous composition containing organic oxygenate selected from the group consisting of alcohols, glycols and weak acids, including:

(i) a polysulfone membrane as a porous support layer; and (ii) mounted thereon, as a separating layer, a membrane of a blend of polyvinyl alcohol and polyacrylic acid;

said blend being characterized by a weight ratio of polyvinyl alcohol to polyacrylic acid of 0.1–10 and having been cured at 125° C.–225° for 1–30 minutes.

* * * * *

UNITED STATES PATENT AND TRADEMARK OFFICE
CERTIFICATE OF CORRECTION

PATENT NO. : 5,009,783

DATED : April 23, 1991

INVENTOR(S) : Craig R. BARTELS

It is certified that error appears in the above-identified patent and that said Letters Patent is hereby corrected as shown below:

Cover Page, correct the Serial No. of the parent application to read -- 459,619 --;

Column 1, line 6, cancel "pending", insert -- USP 4,971,699 issued November 20, 1990 --;

Line 53, correct the spelling of "the";

Column 3, line 4, correct the spelling of "Bruschke";

Column 4, line 32, -- ether-aromatic -- rather than "etheraromatic";

Column 5, line 14, correct "$\bar{M}^n$" to read -- $M_n$ --; line 15, cancel "101w%, insert -- 10w% --; line 19, after "use", insert -- of lower --; line 51, cancel "of"; line 53, cancel "bY", insert -- by --.

Signed and Sealed this

Twenty-ninth Day of December, 1992

*Attest:*

DOUGLAS B. COMER

*Attesting Officer*  *Acting Commissioner of Patents and Trademarks*